United States Patent

Marko et al.

Patent Number: 5,276,173
Date of Patent: Jan. 4, 1994

[54] METHOD FOR REMOVAL FOR IONIC CHLORIDE FROM HYDROXYL-TERMINATED SILOXANES

[75] Inventors: Ollie W. Marko; Robert D. Steinmeyer, both of Carrollton, Ky.

[73] Assignee: Dow Corning Corporation, Midland, Mich.

[21] Appl. No.: 956,223

[22] Filed: Oct. 5, 1992

[51] Int. Cl.$^5$ .............................................. C07F 7/08
[52] U.S. Cl. ...................................................... 556/459
[58] Field of Search ......................................... 556/459

[56] References Cited

U.S. PATENT DOCUMENTS

| | | | |
|---|---|---|---|
| 4,127,598 | 9/1985 | McEntee | 556/442 |
| 4,962,221 | 10/1990 | Huntress et al. | 556/456 |
| 5,084,588 | 1/1992 | Ochetue et al. | 556/459 U X |
| 5,104,999 | 4/1992 | Satoh | 556/459 U X |

OTHER PUBLICATIONS

Kirk–Othmer, Encyclopedia of Chemical Technology, vol. 15, Third Edition, p. 649, John Wiley & Sons, NY 1979.

*Primary Examiner*—Paul F. Shaver
*Attorney, Agent, or Firm*—William F. Boley

[57] ABSTRACT

The present invention is a method for reducing the ionic chloride content of hydroxyl-terminated siloxanes. The method involves contacting the hydroxyl-terminated siloxanes with a molecular sieve effective in removing residual water from the siloxanes. Since ionic chloride strongly partitions into the water phase, ionic chloride is removed along with the water phase. In a preferred embodiment of the present method as aprotic solvent is employed to facilitate water removal from the hydroxyl-terminated siloxanes.

18 Claims, No Drawings

METHOD FOR REMOVAL FOR IONIC CHLORIDE FROM HYDROXYL-TERMINATED SILOXANES

BACKGROUND OF INVENTION

The present invention is a method for reducing the ionic chloride content of hydroxyl-terminated siloxanes with a molecular sieve effective in removing residual water from the siloxanes. Since ionic chloride strongly partitions into the water phase, ionic chloride is removed along with the water phase. In a preferred embodiment of the present method an aprotic solvent is employed to facilitate water removal from the hydroxyl-terminated siloxanes.

Hydroxyl-terminated siloxanes, for example, hydroxyl-terminated polydimethylsiloxanes and hydroxyl-terminated polymethylphenylsiloxanes are useful as cross-linkers, plasticizers, and intermediates in the silicone industry. These siloxanes are typically prepared by the hydrolysis of dimethyldichlorosilane or methylphenyldichlorosilane respectively. The resultant product is separated from water providing a hydrolyzate mixture comprising cyclic siloxanes. hydroxyl-terminated short-chain siloxanes, and residual water containing ionic chloride. The ionic chloride present in the residual water can facilitate further reaction of the hydroxyl-terminated short-chain siloxanes to higher molecular weight siloxanes, thus reducing the amount of silanol in the hydrolyzate mixture.

From a commercial perspective, it is desirable to provide a hydroxyl-terminated siloxane hydrolyzate with a level of silanol that will remain constant over an extended period of time to provide for shipping and warehousing of the hydrolyzate. Therefore, it is an objective of the present method to reduce the ionic chloride content of a hydroxyl-terminated siloxane hydrolyzate to provide a more stable hydrolyzate. It is a further objective to decrease the ionic chloride content of a hydroxyl-terminated siloxane hydrolyzate without significantly reducing the silanol content or altering the molecular weight distribution of the siloxanes. The inventors have discovered that molecular sieves provide a surprisingly effective means for reducing the ionic chloride of hydroxyl-terminated siloxane hydrolyzates by removing residual water and the ionic chloride entrained therein. The removal of the ionic chloride is effected without altering the silanol content of the siloxanes or the molecular weight distribution.

Molecular sieve zeolites are known to have a high affinity for water and other polar molecules and have been used for drying gases and liquids, Kirk-Othmer, Encyclopedia of Chemical Technology, Vol. 15, Third Edition, p. 649, John Wiley and Sons, N.Y.

McEntee, U.S. Pat. No. B1, 127, 598, Certificate Issued Sep. 10, 1985, teaches a process for removing impurities such as biphenyls from impure silanes and siloxanes. The process comprises contacting the impure silane or siloxane with an adsorbent bed selected from the class consisting of a molecular sieve bed and a charcoal bed such that the impurities are adsorbed on the bed.

Huntress et al., U.S. Pat. No. 4,962,221, issued Oct. 9, 1990, describe a process for reducing residual chloride content of polysiloxane fluids. The process comprises contacting the polysiloxane fluid, containing residual chloride, with selected weakly-basic alkaline metal compounds at a temperature less than 100° C. After an appropriate contact time, the polysiloxane fluid is separated from the solid alkaline metal compounds. In a preferred embodiment of the described process, water is added to the process to facilitate removal of residual chloride.

The described art does not recognize that the ionic chloride content of hydroxyl-terminated siloxanes can be effectively reduced by use of molecular sieves to remove residual water contained in the siloxanes. The high affinity of ionic chloride for the water allows the ionic chloride to be removed from the siloxanes along with the residual water.

SUMMARY OF INVENTION

The present invention is a method for reducing the ionic chloride content of hydroxyl-terminated siloxanes. The method involves contacting the hydroxyl-terminated siloxanes with a molecular sieve effective in removing residual water from the siloxanes. Since ionic chloride strongly partitions into the water phase, ionic chloride is removed along with the water phase. In a preferred embodiment of the present method an aprotic solvent is employed to facilitate water removal from the hydroxyl-terminated siloxanes.

DESCRIPTION OF INVENTION

The present invention is a method for removal of ionic chloride from hydroxyl-terminated siloxanes. The method comprises contacting a mixture comprising hydroxyl-terminated siloxanes described by formula $HO(R^1R^2SiO)_n$, water, and ionic chloride with a molecular sieve, where each $R^1$ is independently selected from a group consisting of alkyls comprising one to 12 carbon atoms, each $R^2$ is independently selected from a group consisting of $R^1$ and aryls, and $n=2$ to 100.

The present method can be conducted in standard reactors for contacting a liquid with a solid. The present method can be conducted as a batch, semi-continuous, or continuous process. The present method can be conducted, for example, in a continuous-stirred tank reactor or in a fixed-bed reactor. It is preferred that the present method by conducted as a continuous process using one or more packed beds of molecular sieves.

Hydroxyl-terminated siloxanes which can be reduced in ionic chloride content by the present process ar described by the formula $HO(R^1R^2SiO)_nH$. Each substituent $R^1$ is independently selected from a group consisting of alkyls comprising one to 12 carbon atoms. Preferred is when each substituent $R^1$ is independently selected from a group consisting of alkyls comprising one to four carbon atoms. The substituent $R^1$ can be, for example, methyl, ethyl, propyl, tert-butyl, and hexyl. Most preferred is when each $R^1$ substituent is methyl. Each substituent $R^2$ is independently selected from a group consisting of $R^1$ and aryls. The substituent $R^2$ can be, for example, methyl, ethyl, propyl, tert-butyl, hexyl, phenyl, tolyl, xylyl, and naphthal. Preferred si when each $R^2$ is independently selected from a group consisting of methyl and phenyl. Most preferred is when $R^2$ is selected from a group consisting of methyl and phenyl and each $R^2$ is the same, that is all $R^2$ are either methyl or phenyl. The value n can be within a range of two to 100. Preferred is when n is a value within a range of two to 20.

The hydroxyl-terminated siloxanes are present as a mixture with water. The present method is particularly effective for removing residual water remaining in the siloxanes after standard separation techniques for separating water from siloxanes, for example, phase separation by gravity settling, centrifugation, coalescence, and the like. Therefore, it is preferred that the water content of the mixture be less than about 10 weight percent. More preferred is where the water content of the mixture is less than about one weight percent.

The mixture also contains ionic chloride present as a component within the water. By "inner chloride" it is meant all sources of chloride in the water which are titratable with a base. The concentration of ionic chloride in the water is not critical. However, the present method is particularly effective for reducing the ionic chloride content of the hydroxyl-terminated siloxanes to less than about 500 parts per billion (ppb). Therefore, a mixture having an ionic chloride concentration greater than about 500 ppb is preferred.

A molecular sieve is employed in the present method to remove water from the mixture and the ionic chloride contained therein. The molecular sieves useful in the present method are those porous crystalline aluminosilicates typically referred to as zeolites. Representative zeolites useful in the present method are described, for example, in Kirk-Othmer, Encyclopedia of Chemical Technology, Vol. 15, Third Edition. John Wiley and Sons, N.Y. and are incorporated by reference herein. The zeolites contain channels or interconnected voids that are occupied by cations and water molecules. For the present method to effectively remove water from the hydroxyl-terminated siloxane containing mixture, the molecular sieve should be dehydrated prior to use. The molecular sieve can be dehydrated by standard methods, for example, heating or heating under reduced pressure.

The molecular sieve can be natural occurring zeolite, for example, chabazite, mordenite, erionite, faujasite, and chinoptilolite. The molecular sieve can be a synthetic zeolite, for example Types A, X, and Y. Any molecular sieve can be used in the present process which has a pore size and interconnecting channel size adequate to remove water molecules from the mixture containing the hydroxyl-terminated siloxanes and water containing ionic chloride. In general, a molecular sieve having an apparent pore size within a range of about 0.4 nm to 1.2 nm is considered useful in the present method. By "apparent pore size," it is meant that the smaller of the interconnecting channels or the pore of the molecular sieve is within the described range. More preferred is when the molecular sieve has an apparent pore size within a range of about 0.8 nm to 1.1 nm. The most preferred molecular sieve is zeolite Type 13X. The superior effectiveness of zeolite Type 13X in the present invention is surprising, since zeolite Type 13X is reported to have a pore size of about 1.0 nm. The inventors theorize that the residual water in the mixture containing the hydroxyl-terminated siloxanes complexes with the terminal hydroxyls, thus requiring a larger pore size for removal than would be predicted based upon the molecular size of water.

The temperature at which the present process can be conducted is not critical. Generally, any temperature within a range of about 0° C. to 50° C. is considered useful. However for simplicity of the method, ambient temperature is preferred.

The time of contact of the mixture comprising the hydroxyl-terminated siloxanes, water, and ionic chloride with the molecular sieve will depend upon such factors as the type of molecular sieve and the chemical formula of the hydroxyl-terminated siloxanes. Generally, contact times within a range of about one minute to 30 minutes are considered usefully. Shorter contact times may be used, however the amount of water removed may be reduced. Longer contact times may be used if greater removal of water is desired than that achieved within 30 minutes, but his may result in the loss of silanol.

In a preferred embodiment of the present method, an aprotic solvent is added to the mixture. The purpose of the solvent is to dilute the mixture and facilitate contact of the mixture with the molecular sieve. Therefore, the amount of solvent added to the method is that which provides optimal contact of the mixture with the molecular sieve. The optimal amount of solvent will be dependent upon the particular hydroxyl-terminate siloxanes present in the mixture and the molecular sieve employed. The aprotic solvent can be, for example, an alkane or an aromatic solvent. Preferred are those aprotic solvent having a boiling point within a range of about 80° C. to 140° C. the aprotic solvent example, hexane, heptane, toluene, or xylene.

Molecular sieves used in the present method, after saturation with water, may be washed with low chloride content water to reduce the ionic chloride content contained therein, dehydrated as previously described, and reused in the present method.

The following examples are offer to illustrate and demonstrate the effectiveness of the present invention. These examples are not intended to limit the scope of the present claims.

Example 1. The ability of a molecular sieve to reduce the ionic chloride content of hydroxyl-terminated polydimethylsiloxane was evaluated. The evaluation was conducted in a Teflon column containing about 100 g of Type 13X molecular sieve obtained from Coast Engineering Laboratory, Gardena, Calif. The Type 13X molecular sieve is the sodium form of the Type X crystal structure of an alkali metal aluminosilicate. Type 13X molecular sieve is reported by the manufacturer to adsorb molecules with critical diameters up to 1.0 nm.

A hydrolyzate resulting from the acid catalyzed hydrolysis of dimethyldichlorosilane and having the characteristics described in Table 1, was passed through the column containing the molecular sieve. Residence time of the hydrolyzate within the column was about 15 minutes The process was conducted at about 24° C. In one run the hydrolyzate contained about 4 weight percent heptane. In a second run the hydrolyzate was stripped of the heptane before being passed through the column. Each hydrolyzate was tested before (Control) and after being passed through the column (Sieve Treated) for eater content (Water ppm) and for ionic chloride content (Chloride ppb). Each hydrolyzate was also tested before and after being passed through the column by super critical fluid chromatography (SFC) to determine the weight percent silanol (%SiOH), weight-average molecular wight (Mw), and number-average molecular weight (Mn).The results are present in Table 1.

TABLE 1

| Ionic Chloride Removal From Hydroxyl-Terminated Polydimethylsiloxanes by Type 13X Molecular Sieve | | | | | |
|---|---|---|---|---|---|
| Type Hydrolyzate | Water (ppm) | Chloride (ppb) | % SiOH | Mn | Mw |
| hydrolyzate + heptane | | | | | |
| Control | 1700 | 690 | 1.24 | 1378 | 1958 |

TABLE 1-continued

| | Ionic Chloride Removal From Hydroxyl-Terminated Polydimethylsiloxanes by Type 13X Molecular Sieve | | | | |
|---|---|---|---|---|---|
| Type Hydrolyzate | Water (ppm) | Chloride (ppb) | % SiOH | Mn | Mw |
| Sieve Treated Stripped hydrolyzate | 86 | <100 | 1.19 | 1400 | 1970 |
| Control | 1660 | 1070 | 0.90 | 1726 | 2474 |
| Sieve Treated | 316 | 290 | 0.91 | 1757 | 2447 |

The results presented in Table 1 demonstrate the ability of Type 13X molecular sieve to reduce the water content and correspondingly the ionic chloride content of hydroxyl-terminated polydimethylsiloxanes without significantly effecting the hydroxyl content, Mw, or Mn of the siloxanes. The results also demonstrate the benefit of the use of a aprotic solvent in the method.

Example 2. The ability of molecular sieves to reduce the ionic chloride content of hydroxyl-terminated polymethylphenylsiloxane was evaluated. The evaluation was conducted in a Teflon column containing about 100 g of one of the following molecular sieves. Type 4A, which is reported to adsorb molecules with critical diameters up to 0.4 nm; Type LZY-82, having a pore size of 0.8 nm; and Type 13X molecular sieve, as previously described. All molecular sieves were obtained form Coast Engineering Laboratory, Gardens, Calif. A column packed with MgO chips and with MgO powder was also tested for comparison purposes.

The hydroxyl-terminated polymethylphenylsiloxane tested was a hydrolyzate comprising mainly phenylmethyl cyclics (D3 and D4) and short-chain hydroxyl-terminated polymethylphenylsiloxanes (L2-L19). The initial silanol level (—SiOH) of the hydrolyzate was about 8.5 weight percent. A sample of the hydrolyzate was passed through each column at a temperature of about 24° C. and with a residence time of about 5 minutes. The hydrolyzate was analyzed before and after being passed through the column by the test methods described in Example 1. None of the treatments reduced the silanol levels or the phenylmethyl dimer diol level, HO(PhMeSiO)$_2$H, the most reactive silanol containing species in the hydrolyzate. The effects of the treatments on water levels and ionic chloride levels are presented in Table 2.

TABLE 2

| Ability of Drying Agents to Reduce Ionic Chloride Content of Hydroxyl-Terminated Polymethylphenylsiloxanes | | |
|---|---|---|
| Drying Agent | Water ppm | Chloride ppb |
| None | 7200 | 224 |
| MgO Chips | 7450 | 105 |
| MgO Powder | 5100 | 117 |
| Type 4A Sieve | 2100 | N.T.* |
| Type LZY-82 Sieve | 3920 | 160 |
| Type 13X Sieve | 160 | 89 |

*N.T. — Not Tested

The results presented in Table 2 demonstrate the superior ability of Type 13X Sieve to remove water from hydroxyl-terminated polymethylphenylsiloxanes and the corresponding reduction in ionic chloride content of the siloxanes.

We claim:

1. A method for removal of ionic chloride form hydroxyl-terminated siloxanes, the method comprising: contacting a mixture comprising hydroxyl-terminated siloxanes described by formula $$HO(R^1R^2SiO)_nH$$

water, and ionic chloride with a molecular sieve; where each $R^1$ is independently selected from a group consisting of alkyls comprising one to 12 carbon atoms, each $R^2$ is independently selected from a group consisting of $R^1$ and aryls, and n=2 to 100.

2. A method according to claim 1, wherein the molecular sieve has an apparent pore size within a range of about 0.4 nm to 1.2 nm.

3. A method according to claim 1, wherein the molecular sieve has an apparent pore size of about 1.0 nm.

4. A method according to claim 1, wherein $R^1$ is methyl and $R^2$ is methyl.

5. A method according to claim 1, wherein $R^1$ is methyl and $R^2$ is phenyl.

6. A method according to claim 1, wherein n=2 to 20.

7. A method according to claim 1, wherein the molecular sieve has an apparent pore size of about 1.0 nm, $R^1$ is methyl, $R^2$ is methyl, and n=2 to 20.

8. A method according to claim 1, where the molecular sieve has a pore size of abut 1.0 nm, $R^1$ is methyl, $R^2$ is phenyl, and n=2 to 20.

9. A method according to claim 1, where the mixture further comprises an aprotic solvent.

10. A method according to claim 9, where the aprotic solvent is selected from a group consisting of alkane and aromatic solvents.

11. A method according to claim 9, where the aprotic solvent is selected from a group consisting of hexane, heptane, and toluene.

12. A method according to claim 1, where the molecular sieve is Type 13X zeolite.

13. A method according to claim 1, where the molecular sieve is Type 13X zeolite, $R^1$ is methyl, $R^2$ is methyl, n=2 to 20, and the water comprises less than about one weight percent of the mixture.

14. A method according to claim 13, further comprising the pressure of a aprotic solvent.

15. A method according to claim 14, where the aprotic solvent is selected from a group consisting of hexane, heptane, and toluene.

16. A method according to claim 1, where the molecular sieve is Type 13X zeolite, R1 is methyl, R2is phenyl, n=2 to 20, and the water is present at less than about one weight percent of the mixture.

17. A method according to claim 16, where the mixture further comprises an aprotic solvent.

18. A method according to claim 17, where the aprotic solvent is selected from a group consisting of hexane, heptane, and toluene.

* * * * *